(12) United States Patent
Shibata

(10) Patent No.: US 7,871,422 B2
(45) Date of Patent: Jan. 18, 2011

(54) FORCEPS UNIT FOR ENDOSCOPE

(75) Inventor: Hiroaki Shibata, Saitama-ken (JP)

(73) Assignee: Hoya Corporation, Tokyo (JP)

(*) Notice: Subject to any disclaimer, the term of this patent is extended or adjusted under 35 U.S.C. 154(b) by 0 days.

(21) Appl. No.: 11/134,398

(22) Filed: May 23, 2005

(65) Prior Publication Data
US 2005/0261735 A1 Nov. 24, 2005

(30) Foreign Application Priority Data
May 24, 2004 (JP) ............... 2004-152633

(51) Int. Cl.
*A61B 17/00* (2006.01)
(52) U.S. Cl. ..................... 606/205; 606/206
(58) Field of Classification Search ............ 606/49–51, 606/159, 205, 206; 600/564; 604/22, 187
See application file for complete search history.

(56) References Cited

U.S. PATENT DOCUMENTS

| | | | | |
|---|---|---|---|---|
| 5,715,832 | A * | 2/1998 | Koblish et al. | 600/564 |
| 5,820,373 | A * | 10/1998 | Okano et al. | 433/80 |
| 5,820,630 | A * | 10/1998 | Lind | 606/208 |
| 6,086,565 | A | 7/2000 | Ouchi | |
| 6,139,508 | A * | 10/2000 | Simpson et al. | 600/564 |
| 6,464,632 | B1 * | 10/2002 | Taylor | 600/139 |
| 6,506,209 | B2 | 1/2003 | Ouchi | |
| 6,689,122 | B2 | 2/2004 | Yamamoto | |
| 2001/0047124 | A1 | 11/2001 | Yamamoto | |
| 2001/0051812 | A1 * | 12/2001 | Ouchi | 606/205 |
| 2003/0191464 | A1 | 10/2003 | Kidooka | |

(Continued)

FOREIGN PATENT DOCUMENTS

JP 4-146741 5/1992

(Continued)

OTHER PUBLICATIONS

U.S. Appl. No. 11/086,305 to Ouchi, filed Mar. 23, 2005.

(Continued)

*Primary Examiner*—(Jackie) Tan-Uyen T Ho
*Assistant Examiner*—Melissa Ryckman
(74) *Attorney, Agent, or Firm*—Greenblum & Bernstein P.L.C.

(57) ABSTRACT

A forceps unit for an endoscope is provided. The forceps unit includes a flexible sheath, an operating wire placed inside the flexible sheath to be reciprocable in a direction of an axis of the flexible sheath, a pair of forceps end pieces, and two support shafts rotatably supporting the pair of forceps end pieces, respectively. The two support shafts are swaged and fixed to an end support frame provided to a distal end of the flexible sheath so that the pair of forceps end pieces rotatable around the two support shaft will open and close like a beak when the operating wire is operated back and forth. The forceps unit is further provided with a liquid feed channel that is placed inside the flexible sheath in parallel with the operating wire. In this structure, a distal part of the liquid feed channel is placed to pass between the two support shafts so that an outlet of the liquid feed channel will be placed in front of the two support shafts. An outer end part of each of the two support shafts has a cylindrical shape. Further, the outer end part is swaged to the end support frame.

14 Claims, 4 Drawing Sheets

U.S. PATENT DOCUMENTS

2004/0186348 A1   9/2004   Kidooka

FOREIGN PATENT DOCUMENTS

| JP | 6-98140 | 12/1994 |
|---|---|---|
| JP | 11-047135 | 2/1999 |
| JP | 11-342135 A | 12/1999 |
| JP | 2001-321386 A | 11/2001 |
| JP | 2001-327512 | 11/2001 |

OTHER PUBLICATIONS

English language Abstract of JP 11-047135.
English language Abstract of JP 11-342135 A; Dec. 14, 1999.
English language Abstract of JP 2001-321386 A; Nov. 20, 2001.

\* cited by examiner

US 7,871,422 B2

FORCEPS UNIT FOR ENDOSCOPE

INCORPORATION BY REFERENCE

This application claims priority of Japanese Patent Application No. 2004-152633, filed on May 24, 2004, the entire subject matter of the applications is incorporated herein by reference thereto.

BACKGROUND OF THE INVENTION

The present invention relates to a forceps unit for an endoscope to be inserted into an instrument-inserting channel of an endoscope and used for blood stanching, collecting tissue samples, etc.

A forceps unit for an endoscope is generally formed by swaging and fixing a support shaft (rotatably supporting a pair of forceps end pieces) to an end support frame provided to the distal end of a flexible sheath so that the pair of forceps end pieces rotatable around the support shaft will open and close like the beak of a bird when operating wires, placed inside the flexible sheath to be reciprocable in the direction of the axis of the flexible sheath, are operated back and forth.

In actual use of such a forceps unit for an endoscope, there are cases where it is necessary to squirt cleaning liquid onto mucous membrane to wash blood or unclean liquid away, squirt coloring liquid onto mucous membrane to easily discriminate between normal membrane and abnormal membrane, etc. before the intended blood stanching, collecting tissue samples, etc.

To meet the requirements, there have been proposed forceps units for endoscopes capable of discharging cleaning liquid, coloring liquid, etc. from the tip of the flexible sheath by using the space inside the flexible sheath as a liquid feed channel. An example of such a forceps unit is disclosed in each of Japanese Patent Publication No. HEI06-98140, Japanese Patent Provisional Publication No. HEI 04-146741, and Japanese Patent Provisional Publication No. 2001-327512.

SUMMARY OF THE INVENTION

However, in the forceps units for endoscopes described in the above documents, the liquid discharged from the tip of the flexible sheath hits the support shaft or drive arms of the forceps end pieces supported by the support shaft and thereby flies sideward or obliquely. Such forceps units for endoscopes, incapable of cleaning the target part (affected part, etc.) with cleaning liquid with the forceps end pieces directly facing the target part, have been very inconvenient to the operators.

To avoid the problem, it is possible to place the outlet of the liquid feed channel in front of the support shaft, by placing the liquid feed channel inside the flexible sheath in parallel with the operating wires and letting a distal part of the liquid feed channel pass between two support shafts which support the forceps end pieces respectively. However, such a layout does not work well easily since the liquid feed channel is crushed by strong force applied to the support shafts when the support shafts are fixed to the end support frame by swaging.

The present invention is advantageous in that it provides a forceps unit for an endoscope, realizing easy application of liquid (cleaning liquid, coloring liquid, etc.) to a target part when the pair of forceps end pieces (rotating around support shafts respectively and opening and closing like a beak) is directly facing the target part, while also realizing secure fixation of the support shafts to the end support frame by swaging in the assembly process without the risk of crushing the liquid feed channel.

According to an aspect of the invention, there is provided a forceps unit for an endoscope, which is provided with a flexible sheath, an operating wire placed inside the flexible sheath to be reciprocable in a direction of an axis of the flexible sheath, a pair of forceps end pieces, and two support shafts rotatably supporting the pair of forceps end pieces, respectively. The two support shafts are swaged and fixed to an end support frame provided to a distal end of the flexible sheath so that the pair of forceps end pieces rotatable around the two support shaft will open and close like a beak when the operating wire is operated back and forth. The forceps unit is further provided with a liquid feed channel that is placed inside the flexible sheath in parallel with the operating wire. In this structure, a distal part of the liquid feed channel is placed to pass between the two support shafts so that an outlet of the liquid feed channel will be placed in front of the two support shafts. An outer end part of each of the two support shafts has a cylindrical shape. Further, the outer end part is swaged to the end support frame.

With this configuration, liquid (cleaning liquid, coloring liquid, etc.) can easily be squirted into a target part (affected part, etc.) when the pair of forceps end pieces (rotating around the support shafts and opening and closing like a beak) is directly facing the target part. Further, since the outer end part of each support shaft has a cylindrical shape and the outer end part is swaged to the end support frame, the swaging process can be carried out with considerably slighter force, by which the support shafts can be fixed to the end support frame by swaging without the risk of crushing the liquid feed channel in the assembly process.

Optionally, the forceps unit for an endoscope may include a liquid feed channel holder that supports the distal part of the liquid feed channel and is placed between the two support shafts. In this case, the two support shafts supporting the pair of forceps end pieces may be arranged directly on the same axis, and the liquid feed channel holder and the two support shafts may be formed integrally.

Still optionally, the liquid feed channel holder and the two support shafts formed integrally may be made of stainless steel.

Still optionally, the liquid feed channel may be formed by connecting a flexible tube placed inside the flexible sheath and a solid pipe supported by the liquid feed channel holder together in the vicinity of the distal end of the flexible sheath.

In a particular case, the flexible tube may be made of ethylene tetrafluoride resin.

In a particular case, the solid pipe may be a metal pipe.

In a particular case, the metal pipe may be made of stainless steel.

Optionally, a distal end of the solid pipe may be expanded so as to prevent the outlet of the solid pipe from sinking into the liquid feed channel holder.

BRIEF DESCRIPTION OF THE ACCOMPANYING DRAWINGS

The objects and features of the present invention will become more apparent from the consideration of the following detailed description taken in conjunction with the accompanying drawings, in which.

DETAILED DESCRIPTION OF THE EMBODIMENTS

Figure 1:
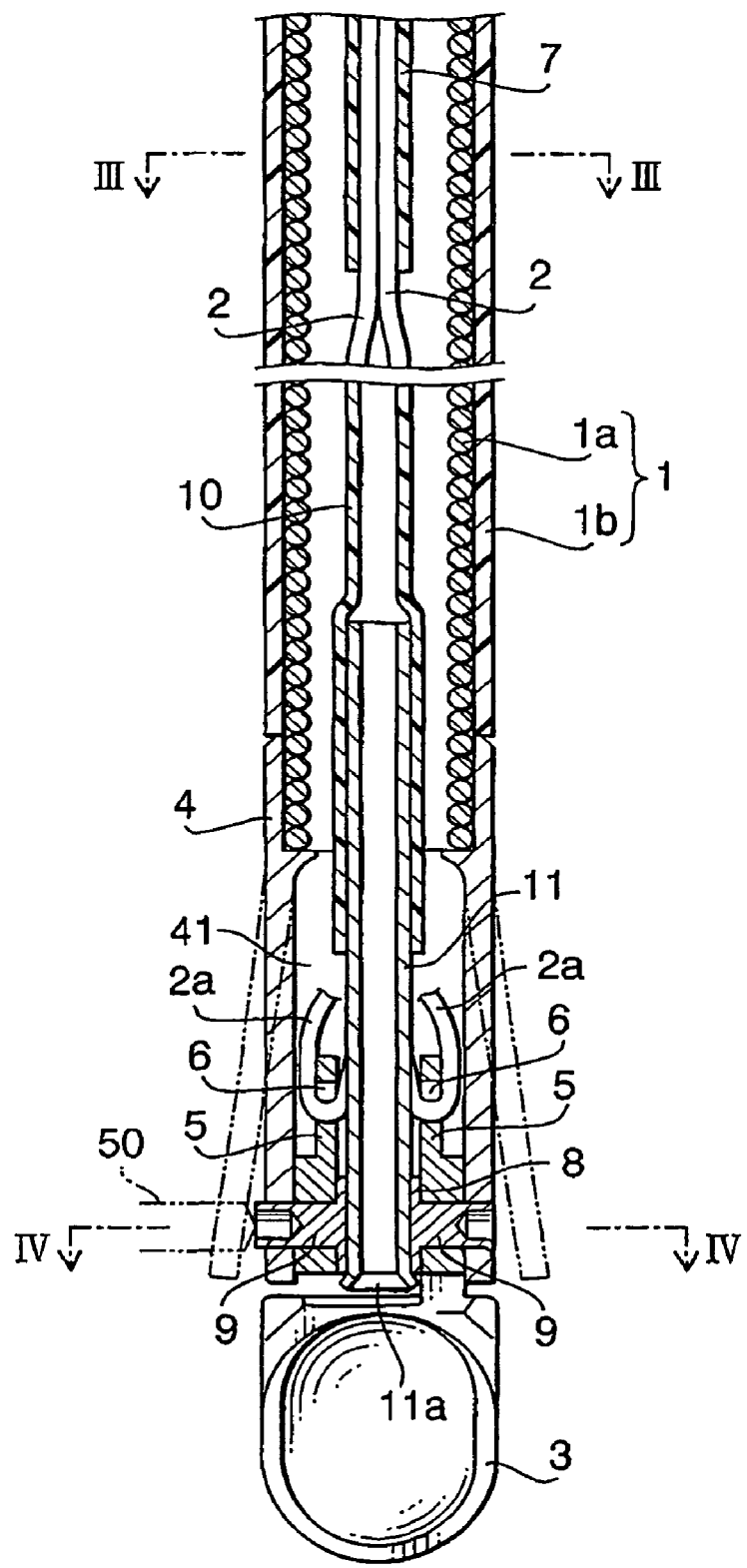
FIG. 1 is a sectional front view of a distal part of a forceps unit for an endoscope in accordance with an embodiment of the present invention.

Referring now to the drawings, a description will be given in detail of a preferred embodiment in accordance with the present invention.

In this embodiment, in a forceps unit for an endoscope (formed by swaging and fixing a support shaft rotatably supporting a pair of forceps end pieces to an end support frame provided to a distal end of a flexible sheath so that the pair of forceps end pieces rotatable around the support shaft will open and close like a beak when operating wires placed inside the flexible sheath to be reciprocable in a direction of an axis of the flexible sheath are operated back and forth), a liquid feed channel is placed inside the flexible sheath in parallel with the operating wires, a distal part of the liquid feed channel is placed to pass between two support shafts supporting the forceps end pieces respectively so that an outlet of the liquid feed channel will be placed in front of the support shafts, an outer end part of each of the support shafts is previously formed in a cylindrical shape, and the outer end part is swaged to the end support frame.

Figure 5:
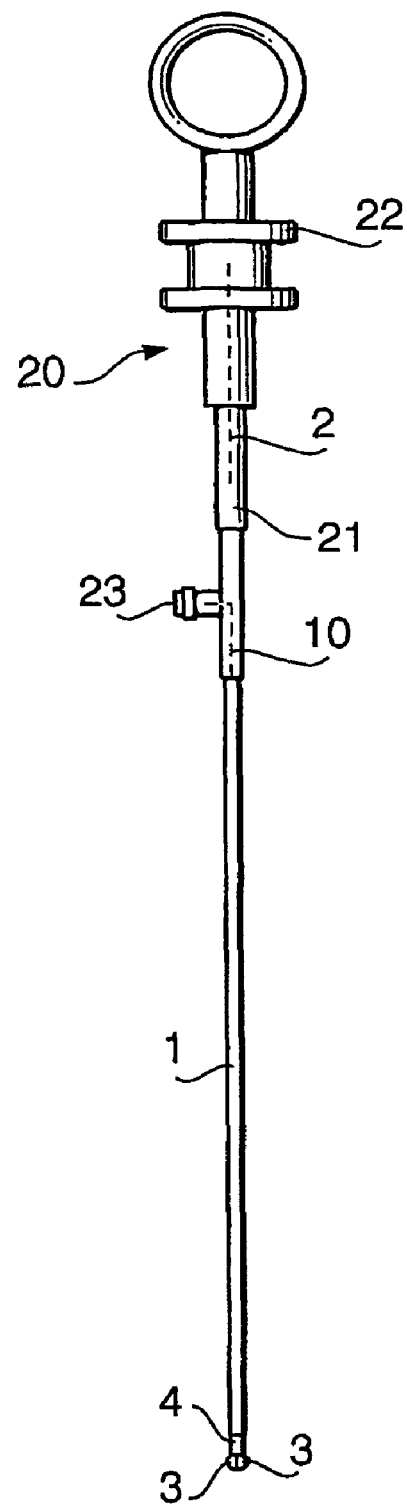
FIG. 5 is a schematic diagram showing the overall composition of the forceps unit.

FIG. 5 is a schematic diagram showing the overall composition of a forceps unit for an endoscope in accordance with an embodiment of the present invention. The forceps unit shown in FIG. 5 is inserted into an instrument-inserting channel of an endoscope and used for blood stanching, collecting tissue samples, etc.

In the forceps unit of FIG. 5, operating wires 2 are inserted into the whole length of a flexible sheath 1 to be reciprocable in the axial direction of the flexible sheath 1. By moving the operating wires 2 in the axial direction at the proximal end of the forceps unit, a pair of forceps end pieces 3 placed at the distal end of the flexible sheath 1 is opened and closed like the beak of a bird.

An operating section 20 at the proximal end of the forceps unit includes a main handle 21 and a sliding handle 22. The main handle 21 is joined to the proximal end of the flexible sheath 1, while the sliding handle 22 is connected to the proximal ends of the operating wires 2. The sliding handle 22 is engaged with the main handle 21 to be freely slidable relative to the main handle 21.

On the lateral face of the main handle 21, a liquid inlet 23 to be used for injecting liquid (cleaning solution, coloring liquid, etc.) into the forceps unit with an unshown injector, etc. is formed to protrude from the lateral face. A liquid feed tube (liquid feed channel) 10 (made of ethylene tetrafluoride resin, for example) connected with the liquid inlet 23 is inserted into the whole length of the flexible sheath 1 in parallel with the operating wires 2.

Figure 2:
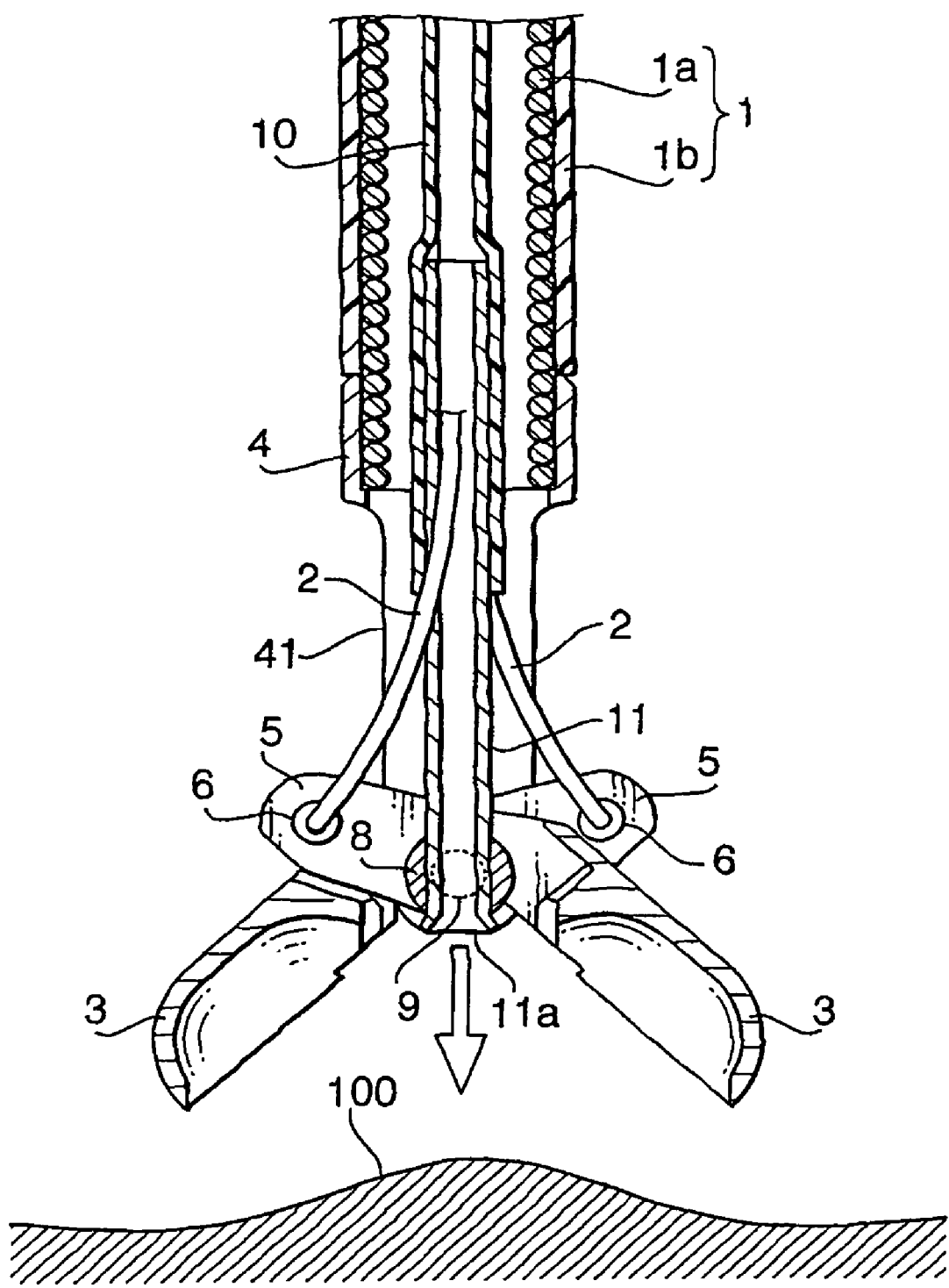
FIG. 2 is a sectional side view of the distal part of the forceps unit.
Figure 3:
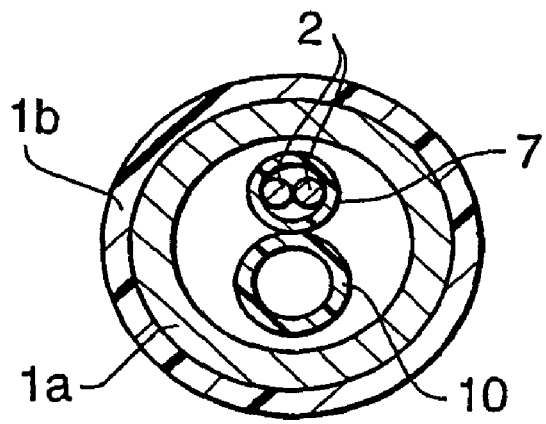
FIG. 3 is a cross-sectional view of the forceps unit taken along the line III-III shown in FIG. 1.
Figure 4:
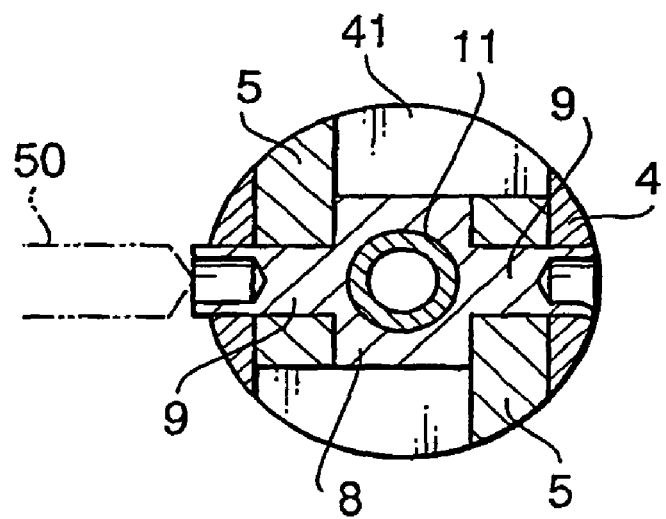
FIG. 4 is a cross-sectional view of the forceps unit taken along the line IV-IV shown in FIG. 1.

FIG. 1 is a sectional front view of a distal part of the forceps unit of this embodiment. FIG. 2 is a sectional side view of the distal part of the forceps unit. FIG. 3 is a cross-sectional view taken along the line III-III shown in FIG. 1. FIG. 4 is a cross-sectional view taken along the line IV-IV shown in FIG. 1. The flexible sheath 1 is formed by covering a coil pipe 1a (made from a stainless steel wire, for example) with a flexible tube 1b made of electrically insulating material. The composition of the flexible sheath 1 is not restricted to the combination of the coil pipe 1a and the flexible tube 1b. For example, the flexible sheath 1 may be made of the coil pipe 1a only, the flexible tube 1b only, etc.

To the tip of the flexible sheath 1, an end support frame 4 is connected and fixed. A distal part of the end support frame 4 is formed in a shape widely separated by a slit 41 as shown in FIG. 1. Drive arms 5, each of which is formed to be integrally connected to the rear of each forceps end piece 3, are placed in the slit 41 as shown in FIG. 1. Each boundary part between each drive arm 5 and each corresponding forceps end piece 3 is supported by each support shaft 9 (fixed in the vicinity of the tip of the end support frame 4 by swaging) to be rotatable.

As the operating wires 2, two wires (stranded wires or solid wires) made of stainless steel are placed inside the flexible sheath 1 along the whole length of the liquid feed tube 10. The tip of each operating wire 2 protrudes from the tip of the flexible sheath 1 and is engaged with each small hole 6 formed in the vicinity of the rear end of each drive arm 5.

Inside the flexible sheath 1, the two operating wires 2 (except their distal parts) are bundled together by a bundling tube 7, as is also shown in FIG. 3 depicting the cross section III-III in FIG. 1.

In the forceps unit configured as above, when the operating wires 2 are operated to reciprocate in the bundling tube 7, the drive arms 5 linked with the operating wires 2 rotate around the support shafts 9 respectively, by which the forceps end pieces 3 (formed integrally with the drive arms 5 respectively) rotate around the support shafts 9 respectively to open and close like the beak of a bird.

The tip of the liquid feed tube 10, reaching the tip of the flexible sheath 1, is connected and fixed to a solid metal pipe 11 (liquid feed channel). The solid metal pipe 11 (made of stainless steel, for example) is placed straight at the position of the central axis of the end support frame 4.

The metal pipe 11 is placed to pass between the support shafts 9 supporting the pair of forceps end pieces 3 as shown in FIG. 1. The outlet 11a of the metal pipe 11 directly faces forward (downward in FIGS. 1 and 2) at a position slightly in front of the support shafts 9 (corresponding to the "throat" of the pair of forceps end pieces 3 like a beak).

With the above configuration, liquid supplied via the liquid feed tube 10 and discharged from the outlet 11a of the metal pipe 11 heads for the space between the pair of forceps end pieces 3 as shown in FIG. 2. Therefore, the liquid (cleaning solution, coloring liquid, etc.) can be correctly squirted into a target part 100 (affected part, etc.) with ease when the pair of forceps end pieces 3 are opened to directly face the target part 100.

The reference numeral "8" in FIGS. 1, 2 and 4 denotes a liquid feed channel holder for holding and fixing the metal pipe 11 on the end support frame 4. The metal pipe 11 is inserted into a through hole of the liquid feed channel holder 8. The distal end of the metal pipe 11 is expanded like a trumpet so as to prevent the outlet 11a of the metal pipe 11 from sinking into the through hole of the liquid feed channel holder 8.

As shown in FIG. 4 depicting the cross section IV-IV in FIG. 1, the two support shafts 9 supporting the pair of forceps end pieces 3 are arranged directly on the same axis to sandwich the liquid feed channel holder 8. In this embodiment, the liquid feed channel holder 8 and the two support shafts 9 are formed integrally as one component made of stainless steel.

Outer ends of the support shafts 9 are inserted into holes of the end support frame 4 respectively and fixed by swaging, by which the integral component (forming the liquid feed channel holder 8 and the two support shafts 9) is securely fixed to the end support frame 4 at its both ends.

Incidentally, when the support shafts 9 are inserted into the holes of the end support frame 4, the distal part of the end support frame 4 (separated by the slit 41) is separated further to widen the slit 41 as indicated by two-dot chain lines in FIG. 1. After the support shafts 9 are inserted into the holes respectively, the distal part of the end support frame 4 is returned to the original straight shape.

In the process for fixing the support shafts 9 to the holes of the end support frame 4 by swaging, if the support shafts 9 have been formed like ordinary rivets and they are swaged to the end support frame 4 by a swaging machine, extremely strong force is applied to the support shafts 9 in their axial direction, by which the liquid feed channel holder 8 is deformed by the support shafts 9 to crush the metal pipe 11.

To avoid the problem, an outer end part of each support shaft 9 is formed in a cylindrical shape and the part is swaged to the end support frame 4. In FIGS. 1 and 4, one of the support shafts 9 on the left-hand side is shown in a state before the swaging process, while the right support shaft 9 is shown in a state after the swaging process.

As above, when the support shafts 9 having the outer end parts formed in the cylindrical shapes are swaged to the end support frame 4, it is unnecessary to apply strong force to the support shafts 9 using a swaging machine. Therefore, the cylindrical part of each support shaft 9 can be swaged to the end support frame 4 by pressing, for example, a handheld electric drill 50 against the cylindrical part to cause plastic deformation.

Incidentally, even in such a swaging process using slight force, it is desirable to previously insert a metal wire, etc. into the distal end of the metal pipe 11 in order to perfectly avoid the crush of the liquid feed channel holder 8 and the metal pipe 11.

As described above, according to the embodiment, liquid (cleaning liquid, coloring liquid, etc.) can easily be squirted into a target part (affected part, etc.) when the pair of forceps end pieces (rotating around the support shafts and opening and closing like a beak) is directly facing the target part. Further, since the outer end part of each support shaft has a cylindrical shape and the outer end part is swaged to the end support frame, the swaging process can be carried out with considerably slighter force, by which the support shafts can be fixed to the end support frame by swaging without the risk of crushing the liquid feed channel in the assembly process.

While a description has been given above of a preferred embodiment in accordance with the present invention, the present invention is not to be restricted by the particular illustrative embodiment and a variety of modifications, design changes, etc. are possible without departing from the scope and spirit of the present invention described in the appended claims.

What is claimed is:

1. A forceps unit for an endoscope, comprising:
   a flexible sheath;
   an operating wire provided within the flexible sheath to be reciprocable in a direction of an axis of the flexible sheath;
   a pair of forceps end pieces;
   two support shafts rotatably supporting the pair of forceps end pieces, respectively, the two support shafts being fixed to an end support frame provided at a distal end of the flexible sheath so that the pair of forceps end pieces rotate around the two support shafts that form an axis to cause the pair of forceps end pieces to rotate about the axis to open and close when the operating wire is operated back and forth; and
   a liquid feed channel that is provided within the flexible sheath in parallel with the operating wire;
   wherein a distal part of the liquid feed channel passes between the two support shafts so that an outlet of the liquid feed channel is positioned in front of the two support shafts, an outer end part of each of the two support shafts has a cylindrical shape, and
   wherein a liquid feed channel holder, that supports a distal end of the liquid feed channel, and said two support shafts comprise a single integral member and a central axis of the two support shafts perpendicularly intersects a central axis of the liquid feed channel when the pair of forceps end pieces are in a closed position,
   wherein the liquid feed channel is formed by a flexible tube placed inside the flexible sheath and a solid pipe supported by the liquid feed channel holder connected together in the vicinity of the distal end of the flexible sheath, and
   wherein a distal end of the solid pipe has an expanded circumference so as to prevent an outlet of the solid pipe from sinking into the liquid feed channel holder, the outlet of the solid pipe being positioned in front of the two support shafts and facing forwarding towards free ends of the forceps end pieces.

2. The forceps unit for an endoscope according to claim 1, wherein the liquid feed channel extends through the liquid feed channel holder between the two support shafts,
   and the two support shafts support the pair of forceps end pieces for rotation about a common axis.

3. The forceps unit for an endoscope according to claim 2, wherein the liquid feed channel holder and the two support shafts are stainless steel.

4. The forceps unit for an endoscope according to claim 1, wherein the flexible tube is made of ethylene tetrafluoride resin.

5. The forceps unit for an endoscope according to claim 1, wherein the solid pipe is a metal pipe.

6. The forceps unit for an endoscope according to claim 5, wherein the metal pipe is made of stainless steel.

7. A forceps unit for an endoscope, comprising:
   a flexible sheath;
   an operating wire provided within the flexible sheath;
   a pair of forceps end pieces;
   two support shafts rotatably supporting the pair of forceps end pieces, respectively, the pair of forceps end pieces rotating around the two support shafts that form an axis to cause the pair of forceps end pieces to rotate about the axis to open and close when the operating wire is moved back and forth;
   a liquid feed channel provided within the flexible sheath in parallel with the operating wire; and
   a liquid feed channel holder that supports a distal part of the liquid feed channel and is positioned between the two support shafts,
   wherein a distal part of the liquid feed channel passes between the two support shafts so that an outlet of the liquid feed channel is positioned in front of the two support shafts, and
   wherein the liquid feed channel holder and said two support shafts comprise a single integral member and a central axis of the two support shafts perpendicularly intersects a central axis of the liquid feed channel when the pair of forceps end pieces are in a closed position,
   wherein the liquid feed channel is formed by a flexible tube placed inside the flexible sheath and a solid pipe supported by the liquid feed channel holder connected together in the vicinity of the distal end of the flexible sheath, and
   wherein a distal end of the solid pipe has an expanded circumference so as to prevent an outlet of the solid pipe from sinking into the liquid feed channel holder.

8. The forceps unit for an endoscope according to claim 7, wherein the two support shafts support the pair of forceps end pieces for rotation about a common axis.

9. The forceps unit for an endoscope according to claim 7, wherein the liquid feed channel holder and the two support shafts are made of stainless steel.

10. The forceps unit for an endoscope according to claim 7, wherein the flexible tube is made of ethylene tetrafluoride resin.

11. A forceps unit for an endoscope, comprising:
a flexible sheath;
an operating wire provided within the flexible sheath;
an end support frame connected to a distal end of the flexible sheath;
a pair of forceps end pieces;
two support shafts, disposed inside the end support frame, that rotatably support the pair of forceps end pieces, respectively, the pair of forceps end pieces rotating around the two support shafts that form an axis to cause the pair of forceps end pieces to rotate about the axis open and close when the operating wire is operated back and forth; and
a liquid feed channel that is provided inside the flexible sheath in parallel with the operating wire,
wherein a distal part of the liquid feed channel passes between the two support shafts so that an outlet of the liquid feed channel is placed positioned in front of the two support shafts, and
wherein a liquid feed channel holder, that supports a distal end of the liquid feed channel, and said two support shafts comprise a single integral member and a central axis of the two support shafts perpendicularly intersects a central axis of the liquid feed channel when the pair of forceps end pieces are in a closed position,
wherein the liquid feed channel is formed by connecting a flexible tube placed inside the flexible sheath and a solid pipe supported by the liquid feed channel holder together in the vicinity of the distal end of the flexible sheath, and
wherein a distal end of the solid pipe has an expanded circumference so as to prevent an outlet of the solid pipe from sinking into the liquid feed channel holder, the outlet of the solid pipe being positioned in front of the two support shafts and facing forwarding towards free ends of the forceps end pieces.

12. The forceps unit for an endoscope according to claim 11, wherein the liquid feed channel extends through the liquid feed channel holder between the two support shafts, and the two support shafts support the pair of forceps end pieces for rotation about a common axis.

13. The forceps unit for an endoscope according to claim 12, wherein the liquid feed channel holder and the two support shafts are stainless steel.

14. The forceps unit for an endoscope according to claim 11, wherein the flexible tube is made of ethylene tetrafluoride resin.

* * * * *